United States Patent [19]

Joyner et al.

[11] Patent Number: 4,476,250

[45] Date of Patent: Oct. 9, 1984

[54] CATALYTIC PROCESS FOR THE PRODUCTION OF METHANOL

[75] Inventors: Richard W. Joyner, Lightwater; John J. McCarroll, Camberley; Stephen R. Tennison, Weybridge, all of England

[73] Assignee: The British Petroleum Company p.l.c., London, England

[21] Appl. No.: 522,740

[22] Filed: Aug. 12, 1983

[30] Foreign Application Priority Data

Aug. 14, 1982 [GB] United Kingdom ............... 8223453

[51] Int. Cl.³ .................... C07C 27/06; C07C 31/04
[52] U.S. Cl. .................................. 518/715; 518/717; 518/718
[58] Field of Search ................ 518/715, 717, 718

[56] References Cited

U.S. PATENT DOCUMENTS 4,119,656 10/1978 Poutsma et al. ............... 518/715
4,289,710 9/1981 Kaiser ............................. 518/717

OTHER PUBLICATIONS

Ryndin et al., J. of Catalysis, 70, 287–297 (1981).
Poutsma et al., J. of Catalysis, 52, 157–168 (1978).

*Primary Examiner*—Howard T. Mars
*Attorney, Agent, or Firm*—Morgan, Finnegan, Pine, Foley & Lee

[57] ABSTRACT

Methanol is produced by passing CO and $H_2$ over a supported Pd catalyst containing an alkali metal alkaline earth metal, or lanthanide promoter and supported on a carbon support with defined surface area characteristics.

7 Claims, No Drawings

CATALYTIC PROCESS FOR THE PRODUCTION OF METHANOL

This invention relates to a process for the production of methanol by contacting a mixture of carbon monoxide and hydrogen, hereinafter referred to as synthesis gas, with a specified catalyst.

Methanol is a valuable industrial product manufactured from synthesis gas. The dwindling reserves of crude oil, from which synthesis gas is frequently derived and the associated need fully to utilise the remaining natural resources such as coal and the gases, eg. methane potentially available from the exploitation of North Sea oilfields, has stimulated research into the utilisation of synthesis gas which can readily be obtained not only from crude oil but also from both coal and methane gas.

Much of the early work on synthesis gas conversion involved the use as catalysts of the iron group metals, and various metal oxide systems. One general disadvantage of such systems is that catalysts which possess acceptable activity generally tend to be unselective i.e. they produce a wide spectrum of products including both hydrocarbons and oxygenated hydrocarbons having a broad distribution of carbon numbers. This not only complicates the recovery of the desired products but also results in wastage of reactants to undesirable products. On the other hand those catalysts having acceptable selectivity generally have a low activity thereby necessitating recycle of large quantities of unchanged reactants.

It is disclosed in U.S. Pat. No. 4,119,6565 (Poutsma et al.) that methanol may be made from carbon monoxide and hydrogen over a catalyst which consists of palladium on a support. The only supports specifically mentioned are silica gel and alumina. The work on which the patent is based is also described in a paper by Poutsma et al in Journal of Catalysis 52, 157–168 (1978). The catalyst is stated to give high selectivity to methanol. When the reaction was carried out under the normal conditions used for synthesising methanol from CO and $H_2$, the paper in Journal of Catalysis shows that methane is not formed. However the highest rate of methanol formation disclosed is 15.2 mol $l^{-1}hr^{-1}$ at 325° C. and at 8000 psig (ca 55.25 MPa or 552.5 bar). This is a very high pressure.

We have found that the activity of a catalyst of the type described by Poutsma is low. Such catalysts would have insufficient activity to be satisfactory for the commercial scale production of methanol.

U.S. Pat. No. 4,235,798 (Bartley et al) disclose a process in which CO and $H_2$ are passed over a catalyst comprising rhodium in combination with alkali metals and a support material. The support material may be alumina, graphite, graphitized carbon, and activated carbon, and activated carbon, but silica gel is preferred. The addition of alkali metal is said to decrease the formation of methane, and to increase the selectivity to acetic acid. The formation of methanol is not disclosed.

In the process of Poutsma et al there is no problem of methane formation and the formation of acetic acid is undesirable when the object is to maximise the production of methanol. Bartley et al do not disclose anything which is relevant to the production of methanol over a palladium catalyst.

U.S. Pat. No. 151,190 (Murchison et al) discloses the production of hydrocarbons from CO and $H_2$ using a catalyst containing Mo, W, Re, Ru, or Pt, a compound of a Group I or IIA element, and a support which may be carbon. A person who is seeking to maximise the production of methanol will seek to avoid the production of hydrocarbons, as this represents a loss of CO to undesired products which then have to be separated from the reaction mixture. Any person seeking to operate a process for making methanol as taught by Poutsma et al would take care to avoid catalysts such as those taught by Murchison et al, which produce large quantities of hydrocarbons.

Kikuzono et al Faraday Discuss Chem. Soc. 1982 72, 135-43 disclose the reaction of CO and $H_2$ over Pd catalyst to produce methanol. Table 1 shows that the addition of Na to a Pd/silica catalyst increases the rate of formation of methanol.

We have found that the addition of alkali metal to a $Pd/SiO_2$ catalyst gives some increase in methanol production rate. However the increase in production rate obtained using alkali metal is relatively small and not sufficient to transform a commercially unsatisfactory catalyst into a commercially satisfactory one.

We have now found that by selection of a Group IA or IIA promoter and a specific carbon support it is possible to obtain catalysts which are very much more active for the production of methanol than the catalysts disclosed by Poutsma.

Furthermore we have found that methanol can be made with a high selectivity over the carbon supported catalyst of the present invention even though (1) the prior disclosures relating to methanol production suggest that acid or alkaline metal oxide catalysts give best results (2) carbon catalyst supports have only been disclosed for reactions of CO and $H_2$ giving main products other than methanol, and (3) a catalyst consisting of Pd alone supported on our carbon supports gives much lower activity than a $Pd/SiO_2$ catalyst of the type disclosed by Poutsma.

According to the present invention there is provided a process for the production of methanol comprising passing a feedstock containing hydrogen and carbon monoxide under conditions of temperature and pressure such that conversion to methanol takes place over a catalyst containing palladium metal dispersed on a support characterised in that (1) the catalyst contains a promoter which is an alkali metal alkaline earth metal, or a lanthanide, and
(2) the support is a graphite-containing carbon having
   (a) a basal plane surface area of at least 100 m²/g
   (b) a ratio of BET surface area to basal plane surface area of not more than 5:1
   (c) a ratio of basal plane surface area to edge surface area of at least 10:1.

Catalysts of this general type are disclosed in G.B. No. 1,471,233. These catalysts are disclosed as being useful for the hydrogenation, dehydrogenation and dehydrocyclisation of hydrocarbons. There is nothing in GB No. 1,471,233 which suggests that the catalysts used in the process of the present invention could be used for the production of methanol.

Reference is made in this specification to elements from various groups of the Periodic Table. The Periodic Table referred to is that published by the United Kingdom Patent Office in the Classification Manual for Section C2 of the Patent Office classification dated 1980.

In this specification the term "alkali metal" means the Group IA elements excluding hydrogen and the term "alkaline earth metal" means the group IIA elements excluding beryllium.

The palladium in the activated catalyst is present as the metal, as evidenced by X-ray diffraction. The palladium may be introduced on to the carbon support by impregnating with a solution of a compound of the metal.

The solvent may be a non-aqueous solvent where palladium compounds soluble in the solvent are available. However it is preferred to use water-soluble palladium compounds (e.g. halides) in the form of their aqueous solutions.

The alkali metal, alkaline earth metal, or the lanthanide may be deposited on the catalyst by impregnation with the vapour of the free element or by using the molten metal where this can be done without using very high temperatures. However the difficulties of using molten metal or metal vapour in the preparation of catalysts on a large scale will be apparent to any person skilled in catalyst preparation. It is therefore preferred to introduce the promoters in the form of a compound.

The compound is preferably a water-stable compound i.e. it can be brought into contact with water without decomposition. The most convenient way of depositing the water-stable compound on the carbon support is by impregnation with an aquoues solution, and it is therefore preferred to use water soluble salts. The solubility in water is preferably sufficient to give the required content of promoter in a single impregnation step.

Catalysts may be prepared containing only a single promoter. Alternatively mixtures of promoters may be used.

In order to obtain an active catalyst for use in the process of the present invention the catalyst preparation is carried out in such a way that catalyst poisons are not left on the catalyst. Chloride ion is believed to adversely affect the activity of the catalyst. Therefore the promoters are not deposited on the catalyst as the chloride salts because the chloride cannot then be readily eliminated from the catalyst. Where the catalyst is prepared from a palladium halide then the halogen must be eliminated by reduction before the promoter is introduced. If the palladium is not deposited on the carbon as a halide then the promoter can be deposited before or at the same time as the palladium.

It is believed to be desirable to avoid the use of sulphur and phosphorus containing compounds in the catalyst preparation and use as any liberation of sulphur and/or phosphorus during catalyst preparation and use is likely to adversely affect the activity of the catalyst.

Examples of suitable compounds which can be used to introduce the promoter are the nitrate, nitrite, carbonate, hydrogen carbonate, azide, hydroxide and acetate.

It is preferred to subject the carbon containing the palladium and promoter to a reduction with hydrogen before use rather than relying on any reduction which may take place as a result of contact with the hydrogen in the synthesis gas during the methanol synthesis step.

As explained above it may be necessary to employ two reduction steps in the preparation of the catalyst if the palladium has been deposited as a halide in order to remove the halide before the promoter is introduced.

Any water or other solvent present in the support after the palladium compound or promoter has been deposited is preferably removed before proceeding to the reduction step. This solvent removal may for example be done by heating the catalyst support at temperatures in the range 50° to 150° C.

The reduction steps may be carried out over a moderately wide range of temperature and pressure and hydrogen feed rates (space velocity), provided that the partial pressure of reduction products is kept low and that all reduction products are removed. The reduction steps are preferably carried out in the gas phase.

Examples of suitable temperature for the reduction of the palladium compounds are those in the range of 100° C. to 400° C., preferably 200° C. to 300° C. Examples of suitable temperatures for the reduction of the palladium plus promoter are those in the range 100° C. to 300° C.

Examples of pressures which may be used are those in the range 0.5 to 100 bar (0.05 to 10 mPa), preferably 0.5 to 5 bar (0.05 to 0.5 MPa).

Examples of suitable GHSV are 1000 to 100,000, preferably greater than 10,000.

Optimum reduction conditions can readily be determined by persons skilled in catalyst preparation.

The carbon is preferably in particulate form eg as pellets. The size of the carbon particles will depend on the pressure drop acceptable in any given reactor (which gives a minimum pellet size) and reactant diffusion constraint within the pellet (which gives a maximum pellet size). The preferred minimum pellet size is 0.5 and the preferred maximum is 5 mm.

The carbons are preferably porous carbons. With the preferred particle sizes the carbons will need to be porous to meet the preferred surface area characteristics.

Carbons may be characterised by their BET, basal plane, and edge surface areas. The BET surface area is the surface area determined by nitrogen adsorption using the method of Brunauer Emmettt and Teller J. Am. Chem. Soc. 60,309 (1938). The basal plane surface area is the surface area determined from the heat of adsorption on the carbon of n-dotriacontane from n-heptane by the method described in Proc.Roy.Soc. A314 pages 473–498, with particular reference to page 489. The edge surface area is the surface area determined from the heat of adsorption on the carbon of n-butanol from n-heptane as disclosed in the Proc.Roy.-Soc. article mentioned above with particular reference to page 495.

The preferred carbons for use in the present invention have a basal plane surface area of at least 120 m$^2$/g, more preferably at least 150 m$^2$/g most preferably at least 200 m$^2$/g. The basal plane surface area is preferably not greater than 1000 m$^2$/g.

The ratio of BET to basal plane surface area is preferably not greater than 4:1, most preferably not greater than 3:1.

It is preferred to use carbons with ratios of basal plane surface area to edge surface area of at least 10:1, more preferably at least 20:1, most preferably at least 50:1.

The preferred carbon support may be prepared by heat treating a carbon-containing starting material. The starting material may be an oleophilic graphite e.g. prepared as disclosed in GB 1 168 785 or may be a carbon black.

However oleophilic graphites contain carbon in the form of very fine particles in flake form and are therefore not very suitable materials for use as catalyst supports. We prefer to avoid their use. Similar considerations apply to carbon blacks which also have a very fine particle size.

The preferred materials are activated carbons derived from vegetable materials e.g. coconut charcoal, or from peat or coal. The materials subjected to the heat treatment preferably have particle sizes not less than these indicated above as being prepared for the carbon support. The surface area of the starting material will always be greater than that of the carbon resulting from the heat treatment.

The preferred starting materials have the following characteristics: BET surface area of greater than 100 $m^2/g$, more preferably at least 500 $m^2/g$.

The preferred heat treatment procedure for preparing carbon supports having the defined characteristics, comprise successive (1) heating the carbon in an inert atmosphere at a temperature of from 900° C. to 3300° C., (2) oxidizing the carbon at a temperature between 300° C. and 1200° C., (3) heating in an inert atmosphere at a temperature of between 900° C. and 3000° C.

The duration of the heating in inert gas is not critical. The time needed to heat the carbon to the required maximum temperature is sufficient to produce the required changes in the carbon.

The rate at which the oxidation is carried out is not critical but care must be taken to prevent complete carbon combustion. The oxidation is most desirably carried out using a gas containing molecular oxygen e.g. air or mixtures of oxygen and a gas which is inert under the reaction conditions e.g. nitrogen or an inert (Group O) gas.

The oxidation step is preferably carried out at a temperature in the range 300° and 600° C.

The oxidation is preferably carried out to give a carbon weight loss of at least 10% wt based on weight of carbon subjected to the oxidation step, more preferably at least 15% wt.

The weight loss is preferably not greater than 40% wt of the carbon subjected to the oxidation step, more preferably not greater than 25% wt of the carbon.

The rate of supply of oxidizing agent is preferably such that the desired weight loss takes place over at least 2 hours, more preferably at least 4 hours.

Where an inert atmosphere is required it may be supplied by nitrogen or an inert (Group O) gas.

The quantity of palladium on the catalyst may for example be in the range 0.1 to 50% by weight based on total weight of the catalyst, preferably 1 to 20% by weight, more preferably 2 to 8% by weight of the catalyst.

We believe that the preferred relative quantities of promoter and palladium compound are best expressed as a molar ratio of palladium to promoter metal (which will correspond to the ratio of numbers of atoms). The mole ratio of promoter (expressed as the element) to palladium is preferably within the range 0.2:1 to 6:1, most preferably 2:1 to 3:1.

The relative amounts of palladium and promoter (calculated as the element) may also be expressed as a weight ratio. In general in a given weight of catalyst the weight ratio of promoter to palladium is preferably between 0.0:1 to 4:1.

The concentration of methanol in equilibrium with CO and $H_2$ falls with increasing temperature. Thus although an increase in temperature may increase the activity of the catalyst the production of methanol becomes equilibrium limited at higher temperatures.

The methanol synthesis reaction may for example be carried out at temperatures in the range from 150° to 350°, preferably from 200° to 300° C. and even more preferably from 250° to 300° C.

Increased pressure favours the production of methanol. The catalyst used in the process of the present invention appears to have an activity which is a linear function of hydrogen partial pressure. The activity of the catalyst used in the process of the present invention is independent of CO pressure which is an advantage compared with some known catalysts. Reaction pressure is suitably in the range from 1 to 300 bars, preferably from 30 to 100 bars.

Preferably the gas hourly space velocity (volume of synthesis gas, at STP per volume of catalyst per hour) is greater than $10^3$ vol/vol/hr. Excessively high space velocities result in an uneconomically low conversion.

The catalyst will function effectively at varying $H_2/CO$ molar ratios in the feed gas. Preferred is a $H_2/CO$ ratio between 1:1 and 8:1, most preferred is the stoichiometric ratio for methanol synthesis, viz a $H_2:CO$ ratio of 2:1.

Although the reaction may be carried out batchwise it is preferably carried out in a continuous manner.

The desired product may be recovered from the effluent from the reaction by various means, such as scrubbing and/or distillation. The residual gas which consists mainly of unreacted synthesis gas may be mixed with fresh carbon monoxide and hydrogen to give the required feed ratio and this composite gas then recycled to the reaction.

The invention is illustrated with reference to the following examples.

EXAMPLE 1

The carbon used as the support material for all catalysts in this and further examples was prepared from a commercially available extrudate activated carbon sold by Degussa A. G. Hanau, under the designation BK4. It was in the form of 4 diameter pellets and had typical BET, basal plane and edge surface areas of 950,182 and 31 $m^2.g^{-1}$ respectively. The ratio of BET to basal plane surface areas was 5.38:1 and the ratio of basal plane to edge surface area was b 5.87:1. The carbon was heat treated as follows:

(1) It was treated from room temperature in an inert temperature to 1700° C. over a period of 4 hours. When the temperature reached 1700° C. the carbon was allowed to cool in the stream of nitrogen to room temperature.

(2) It was then heated in air in a rotating drier furnace at about 520° C. for a time known from experience (about 4 hours) to give a weight loss of 20%.

(3) It was then heated over a period of 4 hours to 1850°0 C. in an inert atmosphere as described in (1) above.

After the three heat treatment stages the carbon had the following surface area properties:
Basal plane surface area (bpsa): 390 $m^2.g^{-1}$
BEt surface area (BETsa): 650 $m^2.g^{-1}$
Edge surface area (esa): 2.3 $m^2.g^{-1}$
Ratio of BET/basal plane surface areas: 1.67:1. Ratio of basal plane/edge surface areas: 170:1.

Before impregnation the carbon support material was acid washed by refluxing 50 g quantities of carbon in 200 $cm^3$ of 5% vol.HCl in water for 3 hours. It was then washed in distilled water followed by drying in a vacuum oven at 100° C. for at least 24 hours.

Four of the catalysts were prepared by impregnating the support with an aqueous acidic solution of $PdCl_2$ and evaporating the water. They were then dried in a vacuum oven for at least 16 hours at 100° C. They were reduced in a flowing stream of hydrogen at 200° C. for 3 hours. The alkali metals Li, Na, K and Cs were then impregnated from aqueous solutions of their nitrates by evaporating the water. The final catalysts were dried in a vacuum oven at 100° C. for at least 16 hours and had the following compositions by weight:
(i) 7.7% Pd/1.5% Li/carbon
(ii) 7.5% Pd/4.9% Na/carbon
(iii) 7.2% Pd/8.0% K/carbon
(iv) 5.7% Pd/25.3% Cs/carbon The catalysts were then reduced in situ in the reactor under 5% $H_2$/He at more than 3000 $hr^{-1}$ space velocity and less than 10 psig (ca 0.17 MPa absolute). The temperature was increased to 300° C. at 60° C. $hr^{-1}$ and then held at 300° C. for 5 hours before cooling to 200° C. ready for synthesis gas introduction.

Catalysts activities were then tested in a one through isothermal micro-reactor at a pressure of 9.3 bar absolute (0.93 MPa) in an $H_2$:CO feed ratio of 2:1. Catalyst bed volumes of 2.2 $cm^3$ were used in a GHSV of 1640 $hr^{-1}$.

The activities obtained are shown in Table 1.

TABLE 1

| Catalyst | Temperature °C. | % Methanol in Effluent | CO Conversion % | Productivity $g.mol.l^{-1}.hr^{-1}$ |
|---|---|---|---|---|
| Pd/Li | 230 | 0.80 | 2.36 | 0.586 |
|  | max activity at 254° C. | 1.13 | 3.32 | 0.827 |
| Pd/Na | 230 | 1.50 | 4.37 | 1.098 |
|  | max activity at 243° C. | 1.83 | 5.30 | 1.400 |
| Pd/K | 230 | 1.08 | 3.17 | 0.791 |
|  | max activity at 248° C. | 1.52 | 4.43 | 1.113 |
| Pd/Cs | 230 | 0.55 | 1.63 | 0.403 |
|  | max activity at 258° C. | 1.07 | 3.14 | 0.783 |

The selectivities to methanol were greater than 98%, the minor products being $CO_2$, $CH_4$, $H_2O$ and ethanol.

EXAMPLE 2

A range of water soluble salts were used for the alkali metal impregnation step. The catalysts were prepared as described in Example 3. The approximate catalyst loadings were 7.2 wt% Pd/8.0 wt%K/carbon. The catalysts were made using $KNO_3$, $KNO_2$, $KN_3$, KOH, $K_2CO_3$, $KHCO_3$, $KCOOCH_3$.

The catalysts were reduced under synthesis gas at 9.3 bar absolute (0.93 MPa) in the microreactor and 1640 $hr^{-1}$ GHSV by increasing the temperature at 60° C. $min^{-1}$ to 220° C. and holding for 2 hours.

Catalyst activities were tested as described in Example 1 at 230° C. The results obtained are shown in Table 2.

TABLE 2

| Catalyst | % Methanol in effluent | % CO Conversion | Productivity $g.mol.l^{-1}.h^{-1}$ |
|---|---|---|---|
| Pd/$KNO_3$ | 0.38 | 1.13 | 0.278 |
| Pd/$KNO_2$ | 0.25 | 0.75 | 0.183 |
| Pd/$KN_3$ | 0.30 | 0.89 | 0.220 |
| Pd/KOH | 0.36 | 1.07 | 0.264 |
| Pd/$K_2CO_3$ | 0.75 | 2.22 | 0.55 |
| Pd/$KHCO_3$ | 1.20 | 3.51 | 0.879 |
| Pd/$KCOOCH_3$ | 0.12 | 0.36 | 0.088 |
| Pd/KCl | 0.001 | — | — |

Selectivities in all cases were greater than 98% to methanol.

Comparative Test A

The procedures described in Example 2 were carried out except that KCl was used in place of the potassium salts used in Example 2. The results obtained are shown in Table 2. Carrying out the catalyst preparation in such a way as to leave chloride ion, a catalyst poison, on the catalyst will destroy the activity of the catalyst.

EXAMPLE 3

Nitrates of Lanthanide and Group IIa metals were used to promote palladium catalysts. The preparation method of Example 1 was followed. The formulations of the catalysts prepared were:
(i) 7.2% Pd/4.2% Mg/carbon
(ii) 7.2% Pd/8.0% Ca/carbon
(iii) 6.9% Pd/24.0% Ba/carbon
(iv) 6.5% Pd/26.0% La/carbon
(v) 6.5% Pd/26.0% Ce/carbon
(vi) 6.5% Pd/26.0% Yb/carbon The catalysts were reduced and had their activities tested as described in Example 2. The data obtained at 230° C. are given in Table 3.

TABLE 3

| Catalyst | % methanol in effluent | CO Conversion % | Productivity $g.mol.l^{-1}.hr^{-1}$ | Methanol Selectivity % |
|---|---|---|---|---|
| Pd/Mg | 0.05 | 0.15 | 0.037 | 90 |
| Pd/Ca | 0.40 | 1.20 | 0.293 | 97 |
| Pd/Ba | 0.53 | 1.57 | 0.390 | 98 |
| Pd/La | 0.23 | 0.69 | 0.168 | 98 |
| Pd/Ce | 0.74 | 2.22 | 0.541 | 98 |
| Pd/Yb | 0.40 | 1.20 | 0.292 | 98 |

The other products for the Pd/Mg catalysts were lower hydrocarbons: $CH_4$-9% $C_2H_6$-0.8% $C_3H_6$-0.2%.

Comparative Test B

A silica gel support sold as Davisson 57 material was used to prepare palladium and sodium promoted palladium catalysts. The palladium was impregnated by evaporating to dryness an aqueous solution of $PdCl_2$. It was dried in a vacuum oven at 100° C. for 20 hours and then reduced in flowing hydrogen at 200° C. for 3 hours.

The Na was impregnated onto half the 5% Pd/$SiO_2$ batch by evaporating to dryness an aqueous solution of $NaHCO_3$. The final compositions of the catalysts were:
(i) 4.8 wt% Pd/$SiO_2$
(ii) 4.3 wt% Pd/2.6 wt% Na/$SiO_2$ The catalysts were reduced and had their activities tested at 230° C. as described in Example 1. The results are given in Table 4.

The Pd/$SiO_2$ was a catalyst made according to the disclosure of Poutsma mentioned above, while the Pd/Na/$SiO_2$ catalyst was a catalyst made in accordance with the disclosure of Kiknzono.

TABLE 4

| Catalyst | % Methanol in effluent | CO Conversion % | Productivity $g.mol.l^{-1}.hr^{-1}$ |
|---|---|---|---|
| Pd/$SiO_2$ | 0.076 | 0.23 | 0.055 |
| Pd/Na/$SiO_2$ | 0.092 | 0.28 | 0.067 |

Under similar conditions Pd catalysts on graphitised carbon exhibited the following activities:

(i) 9.1% Pd/carbon less than 0.001 g.mol. $1^{-1}.hr^{-1}$ (not according to the invention)

(ii) 7.5% Pd/4.9% Na/carbon 1.098 g.mol. $1^{-1}.hr^{-1}$ (according to the invention)

Comparative Test B shows that addition of alkali metal gives some improvement in CO conversion and productivity using the known Pd/silica. However the effect is minor. Using a graphitised carbon support in place of silica leads to a catastrophic fall in productivity. The thousandfold increase in methanol productivity resulting from the addition of the promoter is completely surprising.

Comparative Test C

A sample of commercially available 10% Pd/charcoal (Engelhard Limited) was impregnated with 10%K by evaporating an aqueous solution of $KNO_3$ to dryness. The catalyst was then dried in a vacuum oven at 100° C. for 20 hours. The final composition was 8.7% Pd/8.6% K/charcoal.

The catalyst was reduced and had its activity tested as described in Example 2. A selectivity to methanol of greater than 98% was observed. However the productivity was only 0.014 $mol.l^{-1}.h^{-1}$ at 230° C.

EXAMPLE 4

Catalyst (ii) of Example 1 (Pd/Na/carbon) was tested in a once through isomthermal reactor at 55 bar (5.5 MPa) pressure in $H_2:CO=2:1$ synthesis gas.

4.0 mls (1.8 g) of the catalyst was reduced in 10% $H_2$/He by temperature programming (stepped increase in temperature) to 300° C. in 3 hours and then holding at 300° C. for 16 hours. Synthesis gas was then introduced at 200° C. at 55 bar (0.55 MPa). A maximum methanol productivity of 52 g.mol.$1^{-1}.hr^{-1}$ was obtained with a GHSV of 36000 $h^{-1}$ at 302° C. The selectivity was 98% to methanol.

At an inlet GHSV of 7000 $hours^{-1}$ a maximum methanol productivity of 28 g.mol.$1^{-1}.hr^{-1}$ at 285° C. was obtained with 98% selectivity.

We claim:

1. A process for the production of methanol which comprises passing a feedstock containing hydrogen and carbon monoxide under conditions of temperature and pressure such that conversion is to methanol takes place over catalyst containing palladium metal dispersed on a support characterised in that
    (1) the catalyst contains a promoter which is an element of Group IA or IIA of the Periodic Table or is a lanthanide, and
    (2) the support is a graphite-containing carbon having
        (a) a basal plane surface area of at least 100 $m^2/g$
        (b) a ratio of BET surface area to basal plane surface area of not more than 5:1.
        (c) a ratio of basal plane surface area to edge surface area of at least 10:1.

2. A process according to claim 1 wherein the carbon has a basal plane surface area of at least 150 $m^2/g$.

3. A process according to claim 2 wherein the basal plane surface area is at least 200 $m^2/g$.

4. A process according to claim 1 wherein the ratio of BET to basal plane surface area is not more than 3:1.

5. A process according to claim 1 wherein the carbon has a ratio of basal plane to edge surface area of at least 30:1.

6. A process according to claim 1 wherein the catalyst has been prepared by depositing a palladium halide on the carbon, reducing the palladium halide with hydrogen to eliminate halide, and then depositing a salt of the promoter.

7. A process according to claim 5 wherein the palladium halide and the salt of the promoter are each deposited from separate aqueous solutions.

* * * * *

UNITED STATES PATENT AND TRADEMARK OFFICE
CERTIFICATE OF CORRECTION

PATENT NO. : 4,476,250

DATED : October 9, 1984

INVENTOR(S) : Richard William Joyner; John James McCarroll and Stephen Robert Tennison It is certified that error appears in the above-identified patent and that said Letters Patent is hereby corrected as shown below:

Column 9, line 36, "36000 $h^{311}$" should read --36000 $h^{-1}$--.

Signed and Sealed this

Thirtieth Day of July 1985

[SEAL]

Attest:

DONALD J. QUIGG

Attesting Officer     Acting Commissioner of Patents and Trademarks